(12) United States Patent
Rammos et al.

(10) Patent No.: US 11,597,961 B2
(45) Date of Patent: Mar. 7, 2023

(54) **RAPID COLORIMETRIC DIAGNOSTIC TEST FOR *C. DIFFICILE***

(71) Applicant: Qualitic Biotechnology LLC, Atlanta, GA (US)

(72) Inventors: Danae Rammos, Boston, MA (US); Madhumita Baskaran, Johns Creek, GA (US); Pranav Dorbala, Lexington, MA (US); Allison Julie Wong, Jamaica Plain, MA (US)

(73) Assignee: Qualitic Biotechnology LLC, Atlanta, GA (US)

( * ) Notice: Subject to any disclaimer, the term of this patent is extended or adjusted under 35 U.S.C. 154(b) by 55 days.

(21) Appl. No.: 16/855,534

(22) Filed: Apr. 22, 2020

(65) Prior Publication Data

US 2020/0332337 A1 Oct. 22, 2020

Related U.S. Application Data

(60) Provisional application No. 62/837,029, filed on Apr. 22, 2019.

(51) Int. Cl.
  *G01N 33/52* (2006.01)
  *C12Q 1/04* (2006.01)
  *C12Q 1/32* (2006.01)

(52) U.S. Cl.
  CPC ............... *C12Q 1/04* (2013.01); *C12Q 1/32* (2013.01); *G01N 33/521* (2013.01); *C12Q 2304/24* (2013.01)

(58) Field of Classification Search
  CPC ........ C12Q 2304/24; C12Q 1/32; C12Q 1/04; G01N 33/521
  See application file for complete search history.

(56) References Cited

U.S. PATENT DOCUMENTS

| | | |
|---|---|---|
| 2,999,052 A | 9/1961 | Albaum et al. |
| 4,024,021 A | 5/1977 | Stavropoulos et al. |
| 4,297,271 A | 10/1981 | Guthlein et al. |
| 4,533,630 A | 8/1985 | Wilkins et al. |
| 4,960,714 A | 10/1990 | Hadfield et al. |
| 5,358,690 A | 10/1994 | Guirguis |
| 5,773,234 A | 6/1998 | Pronovost et al. |
| 5,965,375 A | 10/1999 | Valkirs |
| 6,127,140 A | 10/2000 | Vidakovic et al. |
| 8,101,362 B2 | 1/2012 | Cockerill, III et al. |
| 8,889,363 B2 | 11/2014 | Braun et al. |
| 9,096,638 B2 | 8/2015 | Paquette et al. |
| 2008/0096189 A1 | 4/2008 | Boone et al. |

OTHER PUBLICATIONS

Borren et al., "The emergence of Clostridium difficile infection in Asia: A systematic review and meta-analysis of incidence and impact," PLoS One, 12(5): e0176797 (2017).

Buckel et al., "Gut Check: Clostridium difficile Testing and Treatment in the Molecular Testing Era," Infection Control & Hospital Epidemiology, 36(2): 217-221 (2015).

Burnham et al., "Diagnosis of Clostridium difficile Infection: an Ongoing Conundrum for Clinicians and for Clinical Laboratories," Clinical Microbiology Reviews, 26(3): 604-630 (2013).

Deshpande et al., "Diagnostic Accuracy of Real-time Polymerase Chain Reaction in Detection of Clostridium difficile in the Stool Samples of Patients With Suspected Clostridium difficile Infection: A Meta-Analysis," Clinical Infectious Diseases, 53(7): e81-e90 (2011).

DuPont et al., "Acute Infectious Diarrhea in Immunocompetent Adults," The New England Journal of Medicine, 370(16): 1532-1540 (2014).

Girinathan et al., "Clostridium difficile glutamate dehydrogenase is a secreted enzyme that confers resistance to H2O2," Microbiology, 160: 47-55 (2014).

Gutierrez et al., "Increased Risk of Functional Gastrointestinal Sequelae Following Clostridium difficile infection among Active Duty United States Military Personnel (1998-2010)," Gastroenterology, 149(6): 1408-1414 (2015).

Heinlen et al., "Clostridium difficile Infection," The American Journal of the Medical Sciences, 340(3): 247-252 (2010).

Herikstad et al., "A population-based estimate of the burden of diarrhoeal illness in the United States: FoodNet, 1996-7," Epidemiology & Infection, 129(1): 9-17 (2002).

McDonald et al., "Clinical Practice Guidelines for Clostridium dfficile Infection in Adults and Children: 2017 Update by the Infectious Diseases Society of America (IDSA) and Society for Healthcare Epidemiology of America (SHEA)," Clinical Infection Diseases, XX(00): 1-48 (2018).

Odman et al., "An enzymatic process to a-ketoglutarate from L-glutamate: the coupled system L-glutamate dehydrogenase/NADH oxidase," Tetrahedron: Asymmetry, 15(18): 2933-2937 (2004).

Onwueme et al., "High prevalence of toxinogenic Clostridium difficile in Nigerian adult HIV patients," Transactions of the Royal Society of Tropical Medicine and Hygiene, 105: 667-669 (2011).

Peng et al., "Advances in the diagnosis and treatment of Clostridium difficile infections," Emerging Microbes & Infections, 7(1): 1-13 (2018).

Pennington., "Microorganism differentation and identification device," C. Diff Quik Chek Complete : 107-113 (2009).

Roldan et al., "Assessing the Burden of Clostridium difficile Infection in Lowand Middle-Income Countries," Journal of Clinical Microbiology, 56(3): e01747-17 (2018).

Rupnik et al., "Clostridium difficile infection: new developments in epidemiology and pathogenesis," Nature Reviews Micrioblogy, 7: 526-536 (2009).

Schechner et al., "A mathematical model of Clostridium difficile transmission in medical wards and a cost-effectiveness analysis comparing different strategies for laboratory diagnosis and patient isolation," PLoS One, 12(2): 1-12 (2017).

(Continued)

*Primary Examiner* — Satyendra K Singh

(74) *Attorney, Agent, or Firm* — Foley Hoag LLP; Lucas P. Watkins; Allison L. Gilder

(57) ABSTRACT

In certain aspects, provided herein are methods and kits for detecting the presence of *C. difficile* in a biological sample. Also provided herein are methods of selecting of identifying a subject that would benefit from *C. difficile* treatment.

15 Claims, 7 Drawing Sheets

(56) References Cited

OTHER PUBLICATIONS

Schott et al., "Evaluation and Management of Diarrhea in the ED," Emergency Medicine: 7-18 (2011).
Solomon et al., "ID Learning Unit: Understanding and Interpreting Testing for Clostridium difficile," Open Forum Infectious Diseases, 1(1): 1-3 (2014).
Sprague et al., "Patient Isolation Precautions: Are They Worth It?," Canadian Respiratory Journal, 2016: Article 5352625 (2016).

RAPID COLORIMETRIC DIAGNOSTIC TEST FOR C. DIFFICILE

RELATED APPLICATIONS

This application claims priority to U.S. Provisional Application 62/837,029, filed Apr. 22, 2019, which is incorporated herein by reference in its entirety.

BACKGROUND

*C. difficile* infection (CDI) is an antibiotic-resistant, intestinal bacterial infection that causes mild to life-threatening diarrhea. In the field of fecal-based diagnostics, researchers have determined a variety of bacterial detection methods, including methods related to gene-amplification, enzyme-linked immunosorbent assay (ELISA), and bacterial culture. In a clinical setting, these techniques have varying levels of applicability, with the main limitation being that they must be performed in a controlled laboratory setting and typically require the patient to provide a stool sample. In addition, bacterial culture and gene amplification techniques such as polymerase chain reaction (PCR) also take hours to produce results and require complex laboratory equipment, and ELISA requires technicians to add multiple reagents to produce results. Thus, there is a need for advancements in fecal diagnostics for improving time to yield results, lowering technical complexity, and making diagnostic testing more accessible at point-of-care.

SUMMARY OF THE DISCLOSURE

The present disclosure provides methods, devices, and kits for rapid detection of bacterial, particularly rapid detection of glutamate dehydrogenase (GDH) forming bacteria (e.g., *C. difficile*) in biological samples comprising fecal matter.

DETAILED DESCRIPTION

General

Provided herein are methods, devices, and kits for detecting *C. difficile* (e.g., *C. difficile* in a biological sample). In some embodiments, the methods comprise applying the biological sample to a paper medium loaded with glutamate and an oxidizing agent. The methods may further comprise applying a solution comprising an electron transfer agent and a tetrazolium salt or dye precursor to the paper medium. If the paper medium shows color or darkens, the sample comprises *C. difficile*.

Provided herein are methods, devices, and kits for identifying a *C. difficile* infection in a subject by isolating a biological sample from the subject, applying a biological sample isolated from the subject with a paper medium loaded with glutamate and an oxidizing agent, and applying a solution comprising an electron transfer agent and a tetrazolium salt or dye precursor to the paper medium. In some embodiments, if the paper medium shows color, the subject is identified as being infected with *C. difficile*.

Provided herein are methods, devices, and kits for selecting a subject for *C. difficile* infection treatment by applying a biological sample isolated from the subject to a paper medium loaded with glutamate and an oxidizing agent, applying a solution comprising an electron transfer agent and a tetrazolium dye precursor salt to the paper medium. If the paper medium shows color, the subject is selected for treatment.

A rapid point-of-care device for the detection of *C. difficile* and other pathogenic bacteria that produce GDH will allow for higher hospital throughput and patient care. With a quick colorimetric screening, contact precautions on patients without the bacteria can be lifted and resources can be used to treat them and other patients.

As an example, this invention may be used in a hospital emergency department. It can be integrated into current protocols for handling patients suspected of bacterial infection. For example, with *C. difficile* infection, current protocols including contact precautions could be employed and healthcare providers could request patients to produce stool samples for testing; however, rather than sending the samples to laboratory analysis, the samples could be placed on this invention at point-of-care for rapid diagnostic testing. While this is the device's projected use, it may also be potentially used for testing in other settings, such as other clinical departments, medical facilities, mobile clinics, laboratories, or nursing homes, and by other users, such as laboratory technicians or patients. Additionally, this device may not require patients to provide stool samples, as specimens may be obtained from rectal exams.

Figure 5:
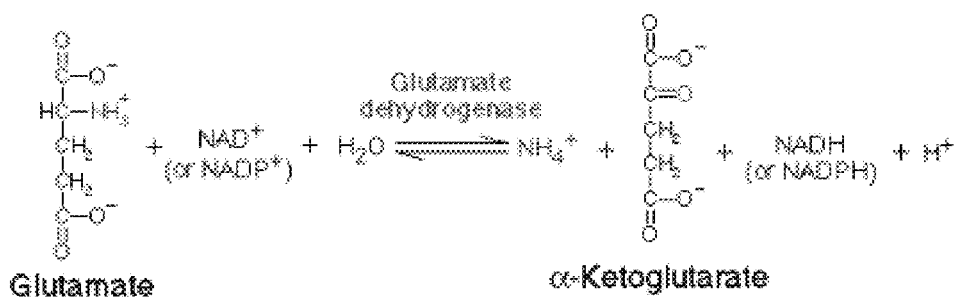
FIG. 5 shows the reaction utilized in the presented device for the reduction of glutamate.

In some embodiments, the compositions, devices, and kits disclosed herein detect glutamate dehydrogenase (GDH)-producing bacteria (e.g., *C. difficile*) by the following mechanism. GDH is an enzyme that catalyzes the conversion of glutamate in a reduction-oxidation reaction to produce alpha-ketoglutarate and NADH, as depicted in FIG. 5. The embodiments disclosed herein encompass systems, devices and methods which involve the reduced and oxidized coenzymes nicotinamide-adenine dinucleotide (NADH, NAD+) or nicotinamide-adenine dinucleotide phosphate (NADPH, NADP+)(collectively herein referred to as NAD(P)H and NAD(P)+). As an example, an indicator or developing solution comprising of phenazine methosulfate and nitroblue tetrazolium, react with NADH by reduction-oxidation and instigate a visible color change. Alternatively, other embodiments may use other combinations of reagents loaded onto the paper medium and indicator solutions that produce color in reduction-oxidation conditions.

Figure 1:
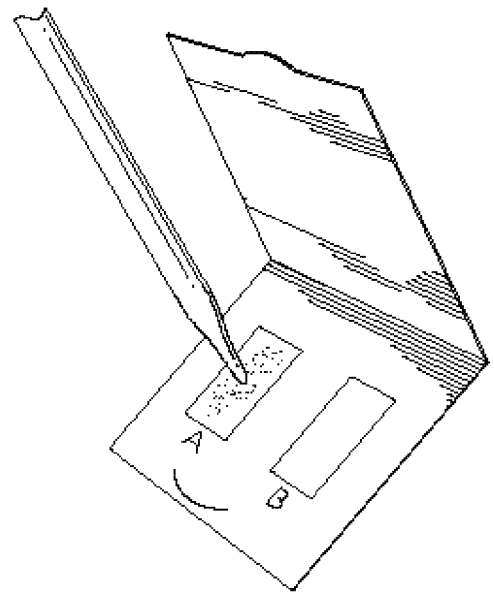
FIG. 1 shows an exemplary mechanism of use of the presented device. The biological sample is applied to the windows in the front of card.
Figure 2:
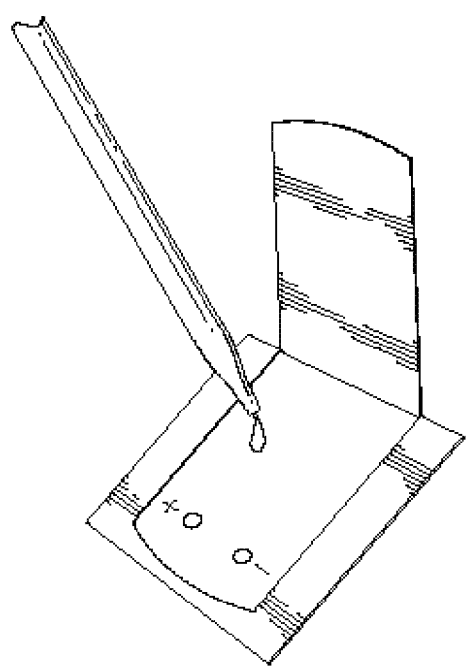
FIG. 2 shows an exemplary mechanism of use of the presented device. Developer solution is added to the back window after card is flipped over.
Figure 3:
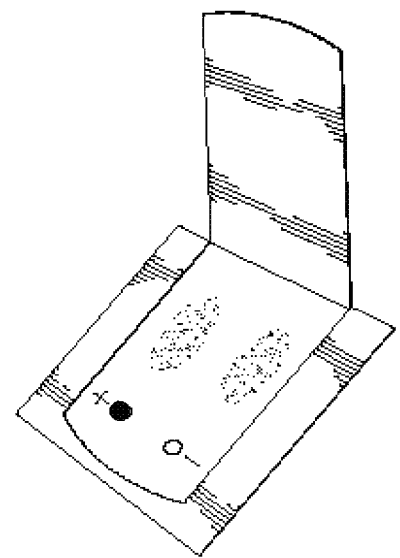
FIG. 3 shows an exemplary mechanism of use of the presented device. Results are displayed. A positive test is shown if both sample windows and positive control are dark (change color).
Figure 4:
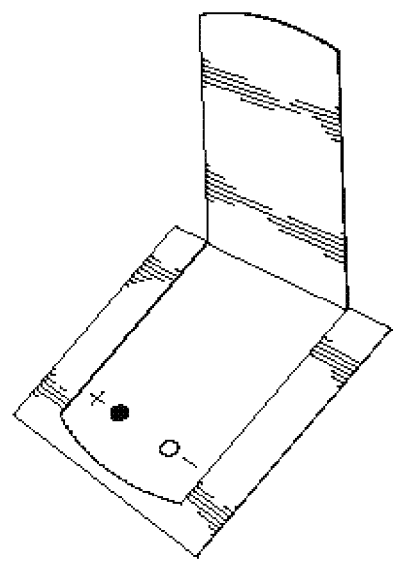
FIG. 4 shows an exemplary mechanism of use of the presented device. Results are displayed. A negative test is shown if both sample windows do not change color or darken while the positive control darkens or changes color.

In one embodiment, the kits and devices described herein use the paper medium loaded with glutamate and NAD+ to be encased by a protective medium. The protective casing may appear as a flat card, as seen in FIG. 1, with flaps to cover the areas on which fecal samples and reagents may be placed. In other embodiments, the casing can take on a more three-dimensional form, such as box-like form where the sample and reagent placement areas will be deeper than the face of the device. The protective medium can be paper or a more rigid material such as plastic, so long as the internal paper is fully covered by it and/or additional packaging.

In some embodiments, the paper medium is loaded with at least 0.0001M, at least 0.0005M, at least 0.001M, at least 0.005M, at least 0.01M, at least 0.05M, at least 0.1M, at least 0.5M, or at least 1.0M glutamate. For example, the paper medium may be loaded with about 0.001M glutamate to about 0.01M glutamate, about 0.005M glutamate to about 0.005M glutamate, about 0.01M glutamate to about 0.1M glutamate, about 0.05M glutamate to about 0.5M glutamate, about 0.5M glutamate to about 1.0M glutamate, or about 0.1M glutamate to 1.0M glutamate. In some embodiments, the paper medium is loaded with at least 0.0001M, at least 0.0005M, at least 0.001M, at least 0.005M, at least 0.01M, at least 0.05M, at least 0.1 M, at least 0.5 M, or at least 1.0M NADP+. For example, the paper medium may be loaded with about 0.001 M NADP+ to about 0.01 M NADP+, about 0.005 M NADP+ to about 0.05 M NADP+, about 0.01 M NADP+ to about 0.1 M NADP+, about 0.05 M NADP+ to about 0.5 M NADP+, or about 0.1 M NADP+ to 1.0 M NADP+.

Provided herein are methods, devices, and kits for detecting *C. difficile* (e.g., *C. difficile*) in a biological sample. In some embodiments, the methods comprise applying the biological sample to a paper medium loaded with glutamate and an oxidizing agent. The methods may further comprise applying a solution comprising an electron transfer agent (e.g., any electron transfer agent disclosed herein) and a tetrazolium dye precursor (e.g., any tetrazolium dye precursor disclosed herein) to the paper medium and, if the paper medium shows color or darkens, the sample comprises *C. difficile*.

In some embodiments, the solution comprises CTC (5-cyano-2,3-ditolyl tetrazolium chloride). The solution may comprise at least 0.1 mM, at least 2 mM, at least 3 mM, at least 4 mM, or at least 5 mM CTC. The solution may comprise about 1 mM to about 3 mM CTC. In other embodiments, the solution comprises about 2 mM to about 5 mM CTC.

Provided herein are methods, devices, and kits for identifying a *C. difficile* infection in a subject by applying a biological sample isolated from the subject to a paper medium loaded with glutamate and an oxidizing agent, applying a solution comprising an electron transfer agent (e.g., any electron transfer agent disclosed herein) and a tetrazolium dye precursor (e.g., any tetrazolium dye precursor disclosed herein) to the paper medium, and, if the paper medium shows color or darkens, the subject is identified as being infected with *C. difficile*.

Provided herein are methods, devices, and kits for selecting a subject for *C. difficile* infection treatment by contacting a biological sample isolated from the subject with a paper medium loaded with glutamate and an oxidizing agent, applying a solution comprising an electron transfer agent (e.g., any electron transfer agent disclosed herein) and a tetrazolium dye precursor (e.g., any tetrazolium dye precursor disclosed herein) to the paper medium, and, if the paper medium shows color, the subject is selected for treatment.

In some embodiments, the glutamate is monosodium glutamate. In some embodiments, an oxidizing agent is nicotinamide-adenine dinucleotide (NAD+) or nicotinamide-adenine dinucleotide phosphate (NADP+). In some embodiments, the tetrazolium dye precursor is nitroblue tetrazolium. The electron transfer agent may be phenazine methosulfate. The paper medium may be filter paper. The biological sample may be a fecal sample (e.g., any biological sample comprising fecal matter, such as a stool sample or a sample from a rectal exam).

The compositions, devices, and kits disclosed herein are designed to detect a wide range of glutamate dehydrogenase amounts and concentrations. In some embodiments, the biological sample comprises at least 0.01 µg, at least 0.02 µg, at least 0.03 µg, at least 0.04 µg, at least 0.05 µg, at least 0.06 µg, at least 0.07 µg, at least 0.8 µg, at least 0.09 µg, at least 0.1 µg, at least 0.2 µg, at least 0.3 µg, at least 0.4 µg, at least 0.5 µg, at least 0.6 µg, at least 0.7 µg, at least 0.8 µg, at least 0.9 µg, at least 1 µg, at least 2 µg, at least 3 µg, at least 4 µg, at least 5 µg, at least 6 µg, at least 7 µh, at least 8 µg, at least 9 µg, at least 10 µg, at least 11 µg, at least 12 µg, at least 13 µg, at least 14 µg, at least 15 µg, at least 16 µg, at least 17 µg, at least 18 µg, at least 19 µg, at least 20 µg, at least 21 µg, at least 22 µg, at least 23 µg, at least 24 µg, at least 25 µg, at least 26 µg, at least 27 µg, at least 28 µg, at least 29 µg, at least 30 µg, at least 31 µg, at least 32 µg, at least 33 µg, at least 34 µg, at least 35 µg, at least 36 µg, at least 37 µg, at least 38 µg, or at least 39 µg glutamate dehydrogenase.

In some embodiments, the biological sample comprises less than 0.01 µg, less than 0.02 µg, less than 0.03 µg, less than 0.04 µg, less than 0.05 µg, less than 0.06 µg, less than 0.07 µg, less than 0.8 µg, less than 0.09 µg, less than 0.1 µg, less than 0.2 µg, less than 0.3 µg, less than 0.4 µg, less than 0.5 µg, less than 0.6 µg, less than 0.7 µg, less than 0.8 µg, less than 0.9 µg, less than 1 µg, less than 2 µg, less than 3 µg, less than 4 µg, less than 5 µg, less than 6 µg, less than 7 µg, less than 8 µg, less than 9 µg, less than 10 µg, less than 11 µg, less than 12 µg, less than 13 µg, less than 14 µg, less than 15 µg, less than 16 µg, less than 17 µg, less than 18 µg, less than 19 µg, less than 20 µg, less than 21 µg, less than 22 µg, less than 23 µg, less than 24 µg, less than 25 µg, less than 26 µg, less than 27 µg, less than 28 µg, less than 29 µg, less than 30 µg, less than 31 µg, less than 32 µg, less than 33 µg, less than 34 µg, less than 35 µg, less than 36 µg, less than 37 µg, less than 38 µg, or less than 39 µg glutamate dehydrogenase.

The *C. difficile* may be any strain that is toxigenic. The *C. difficile* strains and/or ribotypes detected herein may be any hypervirulent strain of *C. difficile*. The *C. difficile* strain may be *difficile* O27. The *Clostridium difficile* may be a *C. difficile* known to cause mild to severe diarrhea or be associated with diarrhea. The *Clostridium difficile* may be a *C. difficile* known to cause or be associated with inflammation of the colon. The *Clostridium difficile* may be a *C. difficile* known to cause or be associated with colitis. The *C. difficile* strain may be *C. difficile* strain R20291 (SM), *C. difficile* strain 196, *C. difficile* strain BI1, *C. difficile* strain M120, *C. difficile* strain M68, *C. difficile* strain 855, or *C. difficile* strain CF5. The *C. difficile* ribotype may be any strain or ribotype listed herein, such as *C. difficile* 001, *C. difficile* 038, *C. difficile* 039, *C. difficile* 002, *C. difficile* 010, *C. difficile* 017, *C. difficile* 012, *C. difficile* 106, *C. difficile*

014/20, *C. difficile* 056, *C. difficile* 003, *C. difficile* 015, *C. difficile* 023, *C. difficile* 053/163, *C. difficile* 078/126, *C. difficile* 310, *C. difficile* 311, *C. difficile* 312, *C. difficile* 308, *C. difficile* 318, *C. difficile* 370, or *C. difficile* 027. The *C. difficile* ribotype may be toxin A positive. The *C. difficile* ribotype may be toxin B positive.

Provided herein are devices (e.g., dry reagent strips, dry strips, paper strips, or paper mediums) and kits for detecting *C. difficile* in a biological sample. In some embodiments, the kit comprises a dry reagent strip, a dry strip, a paper strip, or a paper medium loaded with glutamate and an oxidizing agent, as well as a separate solution (e.g., a developer or indicator solution described herein) comprising an electron transfer agent and a tetrazolium salt or dye precursor. In some embodiments, the kit comprises a dry reagent strip, a dry strip, a paper strip, or a paper medium loaded with glutamate and an oxidizing agent and two additional solutions, one comprising an electron transfer agent and a second solution comprising a tetrazolium salt or dye precursor.

In some embodiments, the oxidizing agent is nicotinamide-adenine dinucleotide (NAD+) or nicotinamide-adenine dinucleotide phosphate (NADP+). In some embodiments, the tetrazolium dye precursor is nitroblue tetrazolium. The electron transfer agent may be phenazine methosulfate. The dry reagent strip, a dry strip, a paper strip, or a paper medium may be filter paper. The biological sample may be a fecal sample (e.g., any biological sample comprising fecal matter, such as a stool sample or a sample from a rectal exam). In some embodiments, the dry reagent strip, dry strip, paper strip, or paper medium comprises two windows for applying a fecal sample. In some embodiments, the dry reagent strip, dry strip, paper strip, or paper medium further comprises a negative control window. In some embodiments, the dry reagent strip, dry strip, paper strip, or paper medium further comprises a positive control window. In some embodiments, the positive control is loaded with GDH. For example, the positive control may comprise at least 0.1 uM, 0.2 uM, 0.3 uM, 0.4 uM, 0.5 uM, 0.6 uM, 0.7 uM, 0.8 uM, 0.9 uM, 1.0 uM, 1.25 uM, 1.5 uM, 1.75 uM, or 2 uM GDH. For example, the positive control may be loaded with about 0.1 uM to about 0.5 uM, about 0.5 uM to 1.0 about uM, about 1.0 uM to about 1.5 uM, about 1.5 uM to about 2.0 uM GDH. The negative control may lack GDH.

*C. difficile* infection (CDI) is an antibiotic-resistant, intestinal bacterial infection that causes mild to life-threatening diarrhea. When hospital patients are suspected of CDI, they are flagged for contact precautions and quarantined until testing proves they are infection-free. Current diagnostic tests for CDI usually take an hour or longer to complete. Additionally, many patients screened annually will not have the disease. The length of diagnostic tests, combined with the volume of over-testing, has a negative impact on hospital efficiency and quality of care. Reducing CDI diagnostic test time can improve throughput and quality of care for both CDI-suspected and other patients in hospitals and clinics around the world.

The devices and kits provided herein include a rapid colorimetric diagnostic test for GDH producing bacteria on a paper medium. The innovative design is lightweight and portable, and the test relies on a single reagent; both of these aspects differentiate it from current tests which require laboratory machinery, trained technicians, and multiple reagents.

In some embodiments, the paper medium is loaded with glutamate and NAD+ or NADP+, and, when exposed to the glutamate dehydrogenase protein (GDH) produced and secreted by *C. difficile*, NAD(P)H is produced, which is detected by the indicator solution within a period of approximately 5 minutes. In some embodiments, the devices and kits provided herein can produce a result in less than 30 minutes, less than 25 minutes, less than 20 minutes, less than 15 minutes, less than 10 minutes, or less than 5 minutes after adding the developer or indicator solution(s) to the device.

In certain embodiments, the kits disclosed herein comprise a paper medium loaded with glutamate (e.g., 0.1M glutamate) and NADP+ (e.g., 0.01M NADP+). The paper medium may also comprise a positive control window loaded with GDH (e.g., 1 uM GDH) and a negative control window that is not loaded with GDH. The kit may further comprise a developer solution comprising CTC (e.g. 3 mM). The developer solution may comprise phenazine methosulfate.

Definitions

For convenience, certain terms employed in the specification, examples, and appended claims are collected here.

The articles "a" and "an" are used herein to refer to one or to more than one (i.e., to at least one) of the grammatical object of the article.

As used herein, the term "administering" means providing an agent or composition to a subject, and includes, but is not limited to, administering by a medical professional and self-administering.

As used herein, the term "subject" means a human or non-human animal selected for treatment or therapy. In certain embodiments, of the methods and compositions described herein the subject is a human subject.

The phrases "therapeutically-effective amount" and "effective amount" as used herein means the amount of an agent which is effective for producing the desired therapeutic effect in at least a sub-population of cells in a subject at a reasonable benefit/risk ratio applicable to any medical treatment.

"Treating" a disease in a subject or "treating" a subject having a disease refers to subjecting the subject to a pharmaceutical treatment, e.g., the administration of a drug, such that at least one symptom of the disease is decreased or prevented from worsening.

*C. difficile* Bacteria

It should be appreciated by those of skill in the art that the disclosed methods, compositions, devices, and kits may be used to detect any strain or ribotype of *C. difficile*.

The *C. difficile* may be and strain that is toxigenic. The *C. difficile* strains and/or ribotypes detected herein may be any hypervirulent strain of *C. difficile*. The *C. difficile* strain may be *C. difficile* O27. The *C. difficile* strain may be *C. difficile* strain restriction endonuclease analysis group BI. The *C. difficile* strain may be *C. difficile* pulse-field gel electrophoresis type NAP1.

The *Clostridium difficile* may be a *C. difficile* known to cause mild to severe diarrhea or be associated with diarrhea. The *Clostridium difficile* may be a *C. difficile* known to cause or be associated with inflammation of the colon. The *Clostridium difficile* may be a *C. difficile* known to cause or be associated with colitis.

The *C. difficile* strain may be *C. difficile* strain R20291 (SM), *C. difficile* strain 196, *C. difficile* strain BI1, *C. difficile* strain M120, *C. difficile* strain M68, *C. difficile* strain 855, or *C. difficile* strain CF5. The *C. difficile* ribotype may be any strain or ribotype listed herein, such as *C. difficile* 001, *C. difficile* 038, *C. difficile* 039, *C. difficile* 002, *C. difficile* 010, *C. difficile* 017, *C. difficile* 012, *C. difficile* 106, *C. difficile* 014/20, *C. difficile* 056, *C. difficile* 003, *C. difficile* 015, *C. difficile* 023, *C. difficile* 053/163, *C. difficile* 078/126, *C.* difficile 310, C. difficile 311, C. difficile 312, C. difficile 308, C. difficile 318, C. difficile 370, or C. difficile 027.

The C. difficile ribotype may be any ribotype that is toxin A positive. The C. difficile ribotype may be any ribotype that is toxin B positive. The C. difficile ribotype may be any ribotype that comprises binary toxin.

Devices and Kits

Provided herein are devices comprising paper strips or other mediums for detecting glutamate dehydrogenase producing bacteria (e.g., C. difficile) in a biological sample. Also provided herein are kits for detecting glutamate dehydrogenase producing bacteria (e.g., C. difficile) in a biological sample. In some embodiments, the kits comprise a paper medium (e.g., any paper medium disclosed herein, such as filter paper) loaded with glutamate and an oxidizing agent (e.g., nicotinamide-adenine dinucleotide (NAD+) or nicotinamide-adenine dinucleotide phosphate (NADP+), or any other agent disclosed herein). The kit may further comprise a solution comprising an electron transfer agent and a tetrazolium dye precursor or salt. In some embodiments, the device is a paper medium (e.g., filter paper or printer paper) loaded with glutamate and an oxidizing agent. The oxidizing agent may be any an oxidizing agent disclosed herein.

Provided herein are devices (e.g., dry reagent strips, dry strips, paper strips, or paper mediums) and kits for detecting C. difficile in a biological sample. In some embodiments, provided herein are kits comprising a dry reagent strip, a dry strip, a paper strip, or a paper medium loaded with glutamate and an oxidizing agent. The kit may also comprise a solution (e.g., a developer or indicator solution) comprising an electron transfer agent and a tetrazolium salt. In some embodiments, the kit comprises two additional solutions rather than one, with a first solution comprising an electron transfer agent and a second solution comprising a tetrazolium dye precursor.

Exemplary embodiments comprise a paper medium loaded with glutamate. The paper medium may be any paper medium that can hold shape after saturation with colored liquid and or demonstrates capillary action, such as filter paper (e.g., Whatman Grade 3 filter paper). The filter paper may be any filter paper the presents a fairly uniform spread of reagent, as well as bleed for colorimetric change to be seen on both sides of the paper medium. In some embodiments, the medium comprises cotton rounds or printer paper.

In some embodiments, the glutamate is any available form of glutamate that can be loaded onto the device mediums described herein. In some embodiments, the glutamate is monosodium glutamate. In some embodiments, the oxidizing agent is nicotinamide-adenine dinucleotide (NAD+) or nicotinamide-adenine dinucleotide phosphate (NADP+). In some embodiments, the tetrazolium dye precursor is nitroblue tetrazolium. The electron transfer agent may be phenazine methosulfate. The tetrazolium dye precursor may be 3-[4,5-dimethylthiazol-2-yl]-2,5-diphenyl tetrazolium bromide (MTT) (which does not require phenazine methosulfate for a color change). The dry reagent strip, a dry strip, a paper strip, or a paper medium may be filter paper. The biological sample may be a fecal sample (e.g., any biological sample comprising fecal matter, such as a stool sample or a sample from a rectal exam).

The device may have two windows for applying a fecal sample. In some embodiments, the device or paper medium further comprises a negative control window and a positive control window. The device may comprise flaps to cover the areas on which biological samples (e.g., fecal samples) and solutions (e.g., solutions described herein) may be placed.

Alternatively, the device can take on a more three-dimensional form, such as box-like form where the sample and solutions placement areas will be deeper than the face of the device. The protective medium can be paper or a more rigid material such as plastic, so long as the internal paper is fully covered by it and/or additional packaging.

Methods

Provided herein are methods of detecting the presence of C. difficile in a biological sample (e.g., a fecal sample or any biological sample comprising fecal matter) using the devices and kits described herein. In some embodiments, the methods disclosed herein comprise contacting the biological sample with a paper medium loaded with glutamate and an oxidizing agent disclosed herein (e.g., nicotinamide adenine dinucleotide (NAD+) or nicotin-amide adenine dinucleotide phosphate (NADP+)). Nicotinamide adenine dinucleotide (NAD+) is a coenzyme found in all living cells. It serves both as a critical coenzyme for enzymes that fuel reduction-oxidation reactions, carrying electrons from one reaction to another, and as a cosubstrate for other enzymes such as the sirtuins and poly(adenosine diphosphateribose) polymerases. Additional examples of oxidizing agents include, but are not limited to, flavin adenine dinucleotide (FAD), flavin mononucleotide (FMN), or pyrrolo-quinoline quinone (PQQ).

The method may further comprise applying a developer or indicator solution(s) comprising an electron transfer agent (e.g., any electron transfer agent disclosed herein) and a tetrazolium dye precursor (e.g., any tetrazolium dye precursor disclosed herein) to the paper medium, and, if the paper medium changes color or darkens, the sample comprises C. difficile.

In some embodiments, the glutamate is monosodium glutamate. In some embodiments, the tetrazolium dye precursor is a tetrazolium salt. The tetrazolium dye precursor may be nitroblue tetrazolium. The electron transfer agent may be phenazine methosulfate.

Also provided herein are methods of identifying a C. difficile infection in a subject, comprising: contacting a biological sample isolated from the subject with a paper medium loaded with glutamate and an oxidizing agent disclosed herein (e.g., nicotinamide adenine dinucleotide (NAD+) or nicotin-amide adenine dinucleotide phosphate (NADP+)).

Tetrazolium compounds are generally very sensitive to strong bases and to light. Thus, special care must be exercised to ensure the integrity of these compounds. Nevertheless, tetrazoliums have played an important role in studies of tissue metabolism. For example, this class of compounds has been used in probing anaerobic oxidation and reduction reactions in cells. The compounds are typically light-colored or colorless compounds that undergo a reduction reaction, in the presence of a reducing agent, to yield a highly colored formazan. Reducing agents such as ascorbates, sulfhydryls, or variants of NADH, NADPH, PQQH$_2$ (reduced PQQ—pyrrolo-quinoline quinone), FMNH$_2$ (reduced FMN—flavin mononucleotide), and FADH$_2$ (reduced FAD—flavin adenine dinucleotide) are capable of forming the dye.

The next step in the dye-forming process is hydride abstraction from the reduced cofactor by an electron transfer agent. Suitable electron transfer agents include enzymes such as diaphorase, lipoic dehydrogenase, ferredoxin-NADP reductase, and lipoamide dehydrogenase. Non-enzymatic electron transfer agents may also be used, such as phenazine methosulfate (PMS), phenazine ethosulfate (PES), 1-methoxyphenazine methosulfate, or Meldola Blue. Reaction kinetics and stability are the primary factors for selecting an electron transfer agent or "hydride abstractor". For example, PMS is the universal hydride abstractor, because it has relatively fast reaction kinetics with most of the tetrazolium compounds listed below.

If GDH is present in the biological sample, the captured hydride is transferred to a tetrazolium compound (dye precursor) to form a colored formazan. Additional exemplary tetrazolium compounds that may be used herein include, but are not limited to, 2-(2'benzothiazolyl)-5-styryl-3-(4'-phthalhydrazidyl) tetrazolium (BSPT), 2-benzothiazolyl-(2)-3,5-diphenyl tetrazolium (BTDP), 2,3-di(4-nitrophenyl) tetrazolium (DNP), 2,5-diphenyl-3-(4-styrylphenyl) tetrazolium (DPSP), distyryl nitroblue tetrazolium (DS-NBT), 3,3'-[3,3'-dimethoxy-(1,1'-biphenyl)-4,4'-diyl]-bis[2-(4-nitrophenyl)-5-phenyl(-2H tetrazolium (NBT), 3-(4,5-dimethyl-2-thiazolyl)-2,5-diphenyl-2H tetrazolium (MTT), 2-phenyl-3-(4-carboxyphenyl)-5-methyl tetrazolium (PCPM), tetrazolium blue (TB), thiocarbamyl nitroblue tetrazolium (TCNBT), tetranitroblue tetrazolium (TNBT), tetrazolium violet, (TV), 2-benzothiazothiazolyl-3-(4-carboxy-2-methoxyphenyl)-5-[4-(2-sulfoethylcarbamoyl)phenyl]-2H-tetrazolium (WST-4), and 2,2'-dibenzothiazolyl-5,5'-bis[4-di(2-sulfoethyl)carbamoylphenyl]-3,3-(3,3-dimethoxy-4,4'-biphenylene)ditetrazolium, disodium salt (WST-5).

The methods, devices, and kits disclosed herein are designed to detect a wide range of glutamate dehydrogenase amounts and concentrations. In some embodiments, the biological sample comprises at least 0.01 µg, at least 0.02 µg, at least 0.03 µg, at least 0.04 µg, at least 0.05 µg, at least 0.06 µg, at least 0.07 µg, at least 0.8 µg, at least 0.09 µg, at least 0.1 µg, at least 0.2 µg, at least 0.3 µg, at least 0.4 µg, at least 0.5 µg, at least 0.6 µg, at least 0.7 µg, at least 0.08 µg, at least 0.9 µg, at least 1 µg, at least 2 µg, at least 3 µg, at least 4 µg, at least 5 µg, at least 6 µg, at least 7 µg, at least 8 µg, at least 9 µg, at least 10 µg, at least 11 µg, at least 12 µg, at least 13 µg, at least 14 µg, at least 15 µg, at least 16 µg, at least 17 µg, at least 18 µg, at least 19 µg, at least 20 µg, at least 21 µg, at least 22 µg, at least 23 µg, at least 24 µg, at least 25 µg, at least 26 µg, at least 27 µg, at least 28 µg, at least 29 µg, at least 30 µg, at least 31 µg, at least 32 µg, at least 33 µg, at least 34 µg, at least 35 µg, at least 36 µg, at least 37 µg, at least 38 µg, or at least 39 µg glutamate dehydrogenase.

The methods, devices, and kits disclosed herein are designed to detect a wide range of glutamate dehydrogenase amounts and concentrations. In some embodiments, the biological sample comprises about 0.01 µg to about 0.05 µg, about 0.03 µg to about 0.08 µg, about 0.05 µg to about 0.1 µg, about 0.1 µg to about 0.5 µg, about 0.3 µg to about 0.8 µg, about 0.5 µg to about 1.0 µg, about 1.0 µg to about 1.5 µg, about 1.5 µg to about 2 µg, about 1 µg to about 5 µg, about 2.5 µg to about 7.5 µg, about 5 µg to about 10 µg, about 7.5 µg to about 12.5 µg, about 10 µg to about 15 µg, about 20 µg to about 25 µg, about 25 µg to about 30 µg, about 30 µg to about 35 µg, about 35 µg to about 40 µg, or about 40 µg to about 45 µg glutamate dehydrogenase.

In some embodiments, the biological sample comprises less than 0.01 µg, less than 0.02 µg, less than 0.03 µg, less than 0.04 µg, less than 0.05 µg, less than 0.06 µg, less than 0.07 µg, less than 0.8 µg, less than 0.09 µg, less than 0.1 µg, less than 0.2 µg, less than 0.3 µg, less than 0.4 µg, less than 0.5 µg, less than 0.6 µg, less than 0.7 µg, less than 0.08 µg, less than 0.9 µg, less than 1 µg, less than 2 µg, less than 3 µg, less than 4 µg, less than 5 µg, less than 6 µg, less than 7 µg, less than 8 µg, less than 9 µg, less than 10 µg, less than 11 µg, less than 12 µg, less than 13 µg, less than 14 µg, less than 15 µg, less than 16 µg, less than 17 µg, less than 18 µg, less than 19 µg, less than 20 µg, less than 21 µg, less than 22 µg, less than 23 µg, less than 24 µg, less than 25 µg, less than 26 µg, less than 27 µg, less than 28 µg, less than 29 µg, less than 30 µg, less than 31 µg, less than 32 µg, less than 33 µg, less than 34 µg, less than 35 µg, less than 36 µg, less than 37 µg, less than 38 µg, or less than 39 µg glutamate dehydrogenase.

In some embodiments, the biological sample comprises at least 0.01 µM, at least 0.02 µM, at least 0.03 µM, at least 0.04 µM, at least 0.05 µM, at least 0.06 µM, at least 0.07 µM, at least 0.8 µM, at least 0.09 µM, at least 0.1 µM, at least 0.2 µM, at least 0.3 µM, at least 0.4 µM, at least 0.5 µM, at least 0.6 µM, at least 0.7 µM, at least 0.08 µM, at least 0.9 µM, at least 1 µM, at least 2 µM, at least 3 µM, at least 4 µM, at least 5 µM, at least 6 µM, at least 7 µM, at least 8 µM, at least 9 µM, at least 10 µM, at least 11 µM, at least 12 µM, at least 13 µM, at least 14 µM, at least 15 µM, at least 16 µM, at least 17 µM, at least 18 µM, at least 19 µM, at least 20 µM, at least 21 µM, at least 22 µM, at least 23 µM, at least 24 µM, at least 25 µM, at least 26 µM, at least 27 µM, at least 28 µM, at least 29 µM, at least 30 µM, at least 31 µM, at least 32 µM, at least 33 µM, at least 34 µM, at least 35 µM, at least 36 µM, at least 37 µM, at least 38 µM, or at least 39 µM glutamate dehydrogenase.

In some embodiments, the biological sample comprises less than 0.01 µM, less than 0.02 µM, less than 0.03 µM, less than 0.04 µM, less than 0.05 µM, less than 0.06 µM, less than 0.07 µM, less than 0.8 µM, less than 0.09 µM, less than 0.1 µM, less than 0.2 µM, less than 0.3 µM, less than 0.4 µM, less than 0.5 µM, less than 0.6 µM, less than 0.7 µM, less than 0.08 µM, less than 0.9 µM, less than 1 µM, less than 2 µM, less than 3 µM, less than 4 µM, less than 5 µM, less than 6 µM, less than 7 µM, less than 8 µM, less than 9 µM, less than 10 µM, less than 11 µM, less than 12 µM, less than 13 µM, less than 14 µM, less than 15 µM, less than 16 µM, less than 17 µM, less than 18 µM, less than 19 µM, less than 20 µM, less than 21 µM, less than 22 µM, less than 23 µM, less than 24 µM, less than 25 µM, less than 26 µM, less than 27 µM, less than 28 µM, less than 29 µM, less than 30 µM, less than 31 µM, less than 32 µM, less than 33 µM, less than 34 µM, less than 35 µM, less than 36 µM, less than 37 µM, less than 38 µM, or less than 39 µM glutamate dehydrogenase.

In some embodiments, the biological sample comprises about 0.01 µg to about 0.05 µg, about 0.03 µM to about 0.08 µM, about 0.05 µM to about 0.1 µM, about 0.1 µM to about 0.5 µM, about 0.3 µM to about 0.8 µM, about 0.5 µM to about 1.0 µM, about 1.0 µM to about 1.5 µM, about 1.5 µM to about 2 µM, about 1 µM to about 5 µM, about 2.5 µM to about 7.5 µM, about 5 µM to about 10 µM, about 7.5 µM to about 12.5 µM, about 10 µM to about 15 µM, about 15 µM to about 20 µM, about 20 µM to about 25 µM, about 25 µM to about 30 µM, about 30 µM to about 35 µM, about 35 µM to about 40 µM, or about 40 µM to about 45 M glutamate dehydrogenase.

Provided herein are methods of selecting a subject for *C. difficile* infection treatment, comprising: contacting a biological sample isolated from the subject with a paper medium loaded with glutamate and an oxidizing agent. The method may further comprise applying a developer or indicator solution(s) comprising an electron transfer agent (e.g., any electron transfer agent disclosed herein) and a tetrazolium dye precursor (e.g., any tetrazolium dye precursor disclosed herein) to the paper medium, and, if the paper medium shows color, the subject is selected for treatment.

Risk factors for *C. difficile*-associated disease (CDAD) comprise those that affect the gut microbial flora, the most common being exposure to antibiotics. Therefore, in some embodiments, the subject has ingested an antibiotic within three months, within one month, within two weeks, or within one week of the onset of symptoms of C. difficile infection. In some embodiments, the subject has dysbiotic gut microflora. Almost all antibiotics have been associated with CDAD. CDAD is a disease predominantly of the aged, but other factors include recent gastrointestinal surgery and immunosuppressive therapy, including cytotoxics. In some embodiments, the subject has recently (e.g., within six months, within three months, within one month) undergone gastrointestinal surgery or immunosuppressive therapy. In some embodiments, the subject has recently (e.g., within six months, within three months, within one month) ingested proton pump inhibitors.

In some aspects, provided herein are methods of detecting C. difficile in a subject and further administering a treatment for C. difficile infection. Standard C. difficile treatments include, but are not limited to, administration of either vancomycin or fidaxomicin. An exemplary dosage regimen is vancomycin 125 mg orally 4 times per day or fidaxomicin 200 mg twice daily for 10 days. Metronidazole may also be used to treat a C. difficile infection. The suggested dosage for metronidazole is, for example, 500 mg orally 3 times per day for 10 days.

Actual dosage levels of the active ingredients in the pharmaceutical compositions or agents to be administered may be varied so as to obtain an amount of the active ingredient (e.g., an agent described herein) which is effective to achieve the desired therapeutic response for a particular patient, composition, and mode of administration, without being toxic to the patient.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician having ordinary skill in the art can readily determine and prescribe the effective amount of the pharmaceutical composition required. For example, the physician could prescribe and/or administer doses of the compounds employed in the pharmaceutical composition at levels lower than that required in order to achieve the desired therapeutic effect and gradually increase the dosage until the desired effect is achieved.

Also provided herein are methods of evaluating whether a C. difficile treatment was successful in eradicating C. difficile from the gastrointestinal tract in a subject. Such methods include utilizing the methods described herein to detect the presence of C. difficile in a biological sample (e.g., a fecal sample or any biological same comprising fecal matter), from a subject that has previously underwent treatment for C. difficile infection. In some embodiments, the methods disclosed herein comprise contacting the biological sample with a paper medium loaded with glutamate and nicotinamide adenine dinucleotide (NAD+) or nicotinamide adenine dinucleotide phosphate (NADP+). The method may further comprise applying a developer or indicator solution(s) comprising an electron transfer agent and a tetrazolium dye precursor to the paper medium, and, if the paper medium changes color, the sample comprises C. difficile, and the treatment was not fully successful. In some embodiments, repeated tests for detecting C. difficile are done over a period of time before, during, and after treatment. In some embodiments, a reduction in the amount of detected C. difficile is an indicator that the treatment is successful, but also that the subject may need another treatment to eradicate the C. difficile infection.

EXEMPLIFICATION

All current C. difficile diagnostics include multiple reagents and are conducted in a laboratory setting. They require custom made nucleotides or antibodies and equipment use that raise the cost of each test. Additionally, even the rapid tests require over 30 minutes to run, not including the time patients take to produce sample or the time it takes to transport the sample to the laboratory. These additional times are highly variable and can take anywhere from a few minutes each to over an hour.

Provided herein is a rapid, colorimetric screening test for C. difficile, such that physicians and nurses can perform point-of-care diagnostics directly, quickly, and efficiently for reducing resource requirements, costs, and patient inconvenience.

The device and kits disclosed herein have the ability to detect C. difficile without putting users at additional infection risk and having the ability to be disposed of easily. Additional features of the embodiments disclosed herein include units that are easily transported and stored, predictive values (positive and negative) over 80%, and ease of use (requiring fewer than 5 steps for completion).

One exemplary embodiment is a paper-based screening device. None of the current C. difficile tests on the market are paper based. Paper-screens, however, have the important benefits of being inexpensive and easy to produce, dispose, and store due to their thin size. Additionally, in the proposed solution, the reaction relies on the GDH enzymes found in C. difficile along with substrates to produce color. No C. difficile diagnostic test currently relies on such enzymatic reactions.

Documentation of an Exemplary Design

Figure 6:
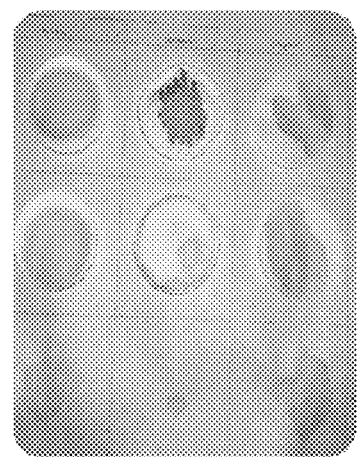
FIG. 6 shows representative images of front, back, and bleed-through for papers tested.

Designing potential devices and kits began with choosing an appropriate filter. Whatman Grade 3 filter paper, cotton rounds, and printer paper were examined as possible media for the screen. As seen in FIG. 6, filter paper held its shape after saturation with colored liquid. Compared to cotton, both filter paper and printer paper demonstrated increased capillary action. This feature is essential for spreading the bacteria across the entire reagent surface. When comparing filter paper and printer paper, filter paper presented a more uniform spread of reagent, as well as optimal bleed for colorimetric change to be seen on both sides of the device.

Once the filter paper was chosen, testing was conducted on the reagents themselves. The initial reaction is a transformation of glutamate into alpha-ketoglutarate by the GDH enzyme. This reaction is rapid and can run at room temperature.

Documentation of the Prototype

Figure 7:
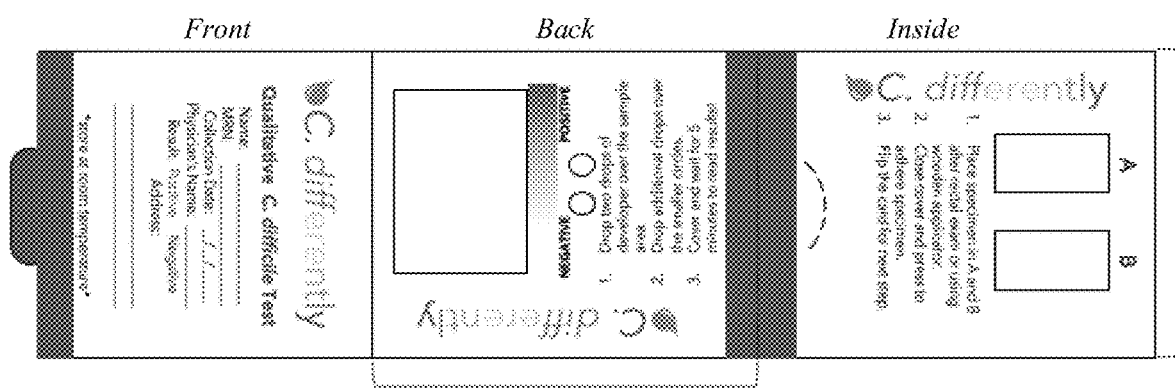
FIG. 7 shows an exemplary device. Final card dimensions when folded are 62×75×1 mm.

One embodiment comprises a paper shell folded over a filter paper. The filter paper is loaded with reagents for the enzyme and is ready to use. FIG. 7 shows the unfolded design that will be folded over the filter.

According to this exemplary embodiment, the filter paper is loaded with 0.1M glutamate and 0.01M NADP+. The filter paper also comprises a positive control window loaded with GDH (e.g., 1 uM GDH) and a negative control window that is not loaded with GDH. The developer solution comprises 3 mM CTC and phenazine methosulfate. C. difficile testing begins with sample collection. The patient can provide a stool sample, or the physician can obtain a sample using a rectal exam. The sample is applied in locations designated as A and B on the inside of the card, as shown in FIG. 7. The front is closed, and the card is flipped to the back where a few drops of developer solution are dropped onto the filter. In 5 minutes, the filter changes color to a dark orange if C. difficile is present in the sample.

Proof of Functionality

To evaluate the functionality of the device, the device's ability to detect GDH enzyme was tested. GDH is secreted by C. difficile, and cultures were found to secrete between 1 and 10 μg. Testing concentrations were chosen based on the 1 and 10 μg range. The 4 experimental concentrations considered were 0.001 μM, 0.01 μM, 0.1 μM and 1 μM which correspond to GDH amounts of 0.03 μg, 0.3 μg, 3 μg and 30 μg, respectively.

Figure 8:
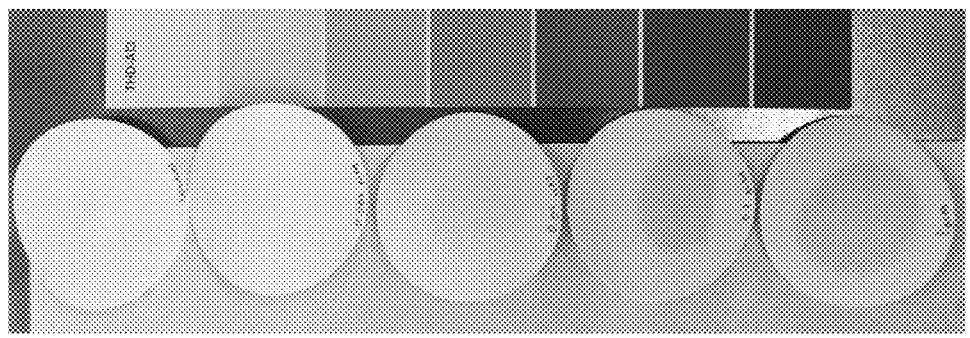
FIG. 8 shows representative images of color change at different GDH concentrations.

The filters were pre-treated with the reaction mixture as the physician would receive them. The aforementioned concentrations, in addition to a 0 μM control, were added to the filters in replicates of 6. The developer solution was then added, and the reaction was allowed to proceed. FIG. 8 shows a representative image of the color achieved by the reaction at the 4 experimental concentrations of GDH. The samples are shown next to a color swatch for visual comparison. The color changes seen at 1 μM and 0.1 μM were considered clear, and even the 0.01 μM was detectable.

Figure 9:
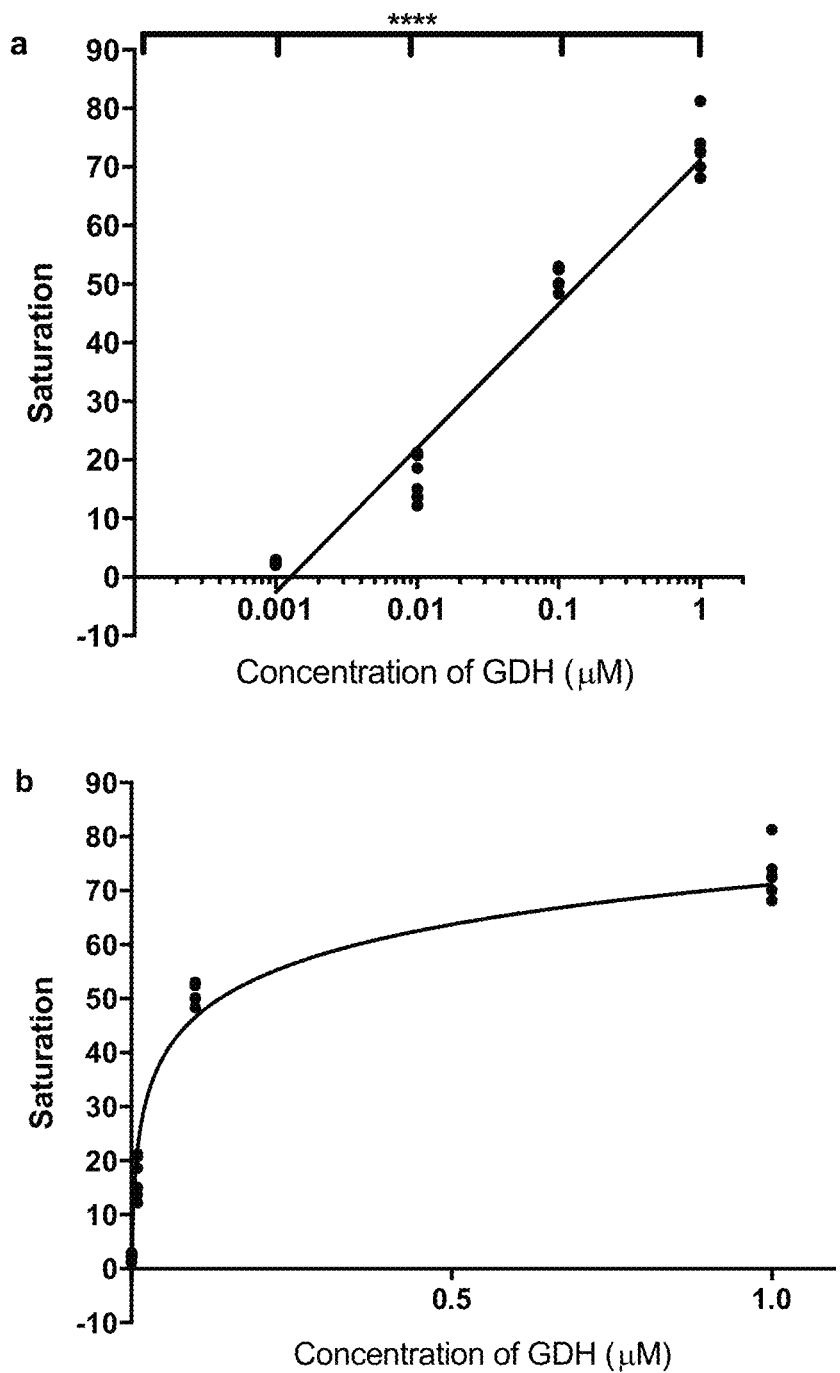
FIG. 9 has two parts, A-B, and shows graphs depicting the saturation of the GDH assay on the filters at varying concentrations of the enzyme. Each concentration was tested in six replicates, and saturation was found via ImageJ on a scale of 0 to 255. X-axis is shown on a logarithmic scale (Part A) and in a linear scale (Part B). **** indicate significance at $p<0.0001$.

All filters were analyzed via ImageJ—an image processing program produced by the National Institutes of Health—to determine the saturation of the color. Saturation was plotted versus GDH concentration and the resulting graph is shown in FIG. 9. FIG. 9, Part A shows the values plotted on a logarithmic x-axis, yielding a linear line of best fit with $r^2=0.9679$. The high degree of linear fit indicates that it is possible to interpolate saturation within this concentration range. Additionally, all the concentrations differed at $p<0.0001$. Since the logarithmic graph could not show the control saturations, the data were also plotted on a linear x-axis (FIG. 9, Part B) to show the control concentrations as well.

Incorporation by Reference

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method of detecting Clostridioides difficile (C. difficilel), comprising:
   (a) applying a fecal sample to a filter paper medium loaded with glutamate, and an oxidizing agent selected from the group consisting of nicotinamide-adenine dinucleotide (NAD+), and nicotinamide-adenine dinucleotide phosphate (NADP+), wherein the filter paper medium comprises a window for direct application of the fecal sample;
   (b) applying a solution comprising an electron transfer agent and a tetrazolium dye precursor to the filter paper medium; and
   (c) detecting C. difficile in the fecal sample colorimetrically based on the activity of glutamate dehydrogenase enzyme of the C. difficile present in the fecal sample.

2. A method of identifying a C. difficile infection in a subject, comprising:
   (a) isolating the fecal sample from the subject; and
   (b) detecting C. difficile in the fecal sample according to the method of claim 1.

3. A method of selecting a subject for C. difficile infection treatment, comprising:
   (a) identifying a C. difficile infection in a subject according to the method of claim 2; and
   (b) if the filter paper medium shows color, selecting the subject for treatment of C. difficile infection.

4. The method of claim 1, wherein the tetrazolium dye precursor is nitroblue tetrazolium.

5. The method of claim 1, wherein the electron transfer agent is phenazine methosulfate.

6. The method of claim 1, wherein the fecal sample comprises 0.3 μg glutamate dehydrogenase.

7. The method of claim 1, wherein the fecal sample comprises 3 μg glutamate dehydrogenase.

8. The method of claim 1, wherein the fecal sample comprises 30 μg glutamate dehydrogenase.

9. The method of claim 1, wherein the C. difficile is C. difficile ribotype O27.

10. A kit for detecting Clostridioides difficile (C. difficile) in a fecal sample, the kit comprising:
    (a) a filter paper medium loaded with glutamate, and an oxidizing agent selected from the group consisting of nicotinamide-adenine dinucleotide (NAD+), and nicotinamide-adenine dinucleotide phosphate (NADP+), wherein the filter paper medium comprises a window for direct application of a fecal sample; and
    (b) a solution comprising an electron transfer agent and a tetrazolium dye precursor;
    wherein the kit is configured to detect the presence of C. difficile in the fecal sample colorimetrically based on the activity of glutamate dehydrogenase enzyme of the C. difficile present in the fecal sample.

11. The kit of claim 10, wherein the tetrazolium dye precursor is nitroblue tetrazolium.

12. The kit of claim 10, wherein the electron transfer agent is phenazine methosulfate.

13. The kit of claim 10, wherein the paper medium comprises two windows for applying a fecal sample.

14. The kit of claim 10, wherein the paper medium further comprises a negative control window.

15. The kit of claim 10, wherein the paper medium further comprises a positive control window.

* * * * *